United States Patent
Yoo et al.

(10) Patent No.: US 11,017,314 B2
(45) Date of Patent: May 25, 2021

(54) METHOD AND DEVICE FOR SEARCHING NEW MATERIAL

(71) Applicant: SAMSUNG ELECTRONICS CO., LTD., Suwon-si (KR)

(72) Inventors: Jiho Yoo, Hwaseong-si (KR); Youngchun Kwon, Suwon-si (KR); Kyungdoc Kim, Suwon-si (KR); Jaikwang Shin, Seoul (KR); Hyosug Lee, Suwon-si (KR); Younsuk Choi, Seongnam-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 1128 days.

(21) Appl. No.: 15/189,373

(22) Filed: Jun. 22, 2016

(65) Prior Publication Data

US 2017/0124482 A1    May 4, 2017

(30) Foreign Application Priority Data

Nov. 4, 2015 (KR) .................. 10-2015-0154676

(51) Int. Cl.
```
G06N 20/00    (2019.01)
G06N 7/00     (2006.01)
G06F 16/245   (2019.01)
G16C 20/30    (2019.01)
G06F 30/20    (2020.01)
G16C 20/70    (2019.01)
```

(52) U.S. Cl.
CPC ........... *G06N 20/00* (2019.01); *G06F 16/245* (2019.01); *G06F 30/20* (2020.01); *G06N 7/005* (2013.01); *G16C 20/30* (2019.02); *G16C 20/70* (2019.02)

(58) Field of Classification Search
CPC ...... G06N 20/00; G06N 7/005; G06F 16/245; G06F 17/5009; G16C 20/30; G16C 20/70
See application file for complete search history.

(56) References Cited

U.S. PATENT DOCUMENTS 6,411,945 B1   6/2002 Nakajima
6,647,342 B2  11/2003 Iglesia et al.
(Continued)

FOREIGN PATENT DOCUMENTS

CN    102819647    12/2012
CN    104007243     8/2014
(Continued)

OTHER PUBLICATIONS

Daniel S Murrell et al, "Chemically Aware Model Builder (camb): an R package for property and bioactivity modelling of small molecules", Aug. 28, 2015, Journal of Cheminformatics 7, Article number: 45, pp. 1-10 (Year: 2015).*

(Continued)

*Primary Examiner* — Kamran Afshar
*Assistant Examiner* — Ying Yu Chen
(74) *Attorney, Agent, or Firm* — Cantor Colburn LLP

(57) ABSTRACT

A method for searching a new material includes: performing a learning on a material model, which is modeled based on a known material; determining a candidate material by inputting a targeted physical property to a result of the learning; and determining the new material from the candidate material.

20 Claims, 6 Drawing Sheets

(56) References Cited

U.S. PATENT DOCUMENTS

| | | | |
|---|---|---|---|
| 8,244,504 B1* | 8/2012 | Jacobs | G16B 15/00 703/2 |
| 9,529,006 B1* | 12/2016 | Ashrafuzzaman | G01N 33/92 |
| 10,152,576 B2 | 12/2018 | Matsuura et al. | |
| 2002/0086791 A1 | 7/2002 | Iglesia et al. | |
| 2003/0059837 A1 | 3/2003 | Levinson et al. | |
| 2003/0059873 A1 | 3/2003 | Meng et al. | |
| 2003/0078740 A1 | 4/2003 | Kieken et al. | |
| 2004/0083083 A1 | 4/2004 | Doganaksoy et al. | |
| 2005/0089923 A9* | 4/2005 | Levinson | G16C 20/30 435/7.1 |
| 2006/0074594 A1 | 4/2006 | Ceder et al. | |
| 2014/0236548 A1 | 8/2014 | Conduit et al. | |
| 2015/0154146 A1 | 6/2015 | Yoo et al. | |
| 2015/0169822 A1 | 6/2015 | Kitano et al. | |

FOREIGN PATENT DOCUMENTS

| | | | |
|---|---|---|---|
| CN | 104603785 | | 5/2015 |
| CN | 104699743 | | 6/2015 |
| EP | 2180435 | A1 | 4/2010 |
| EP | 2881874 | | 6/2015 |
| JP | 6309385 | A | 11/1994 |
| JP | 1055348 | A | 2/1998 |
| JP | 2003058579 | A | 2/2003 |
| JP | 3525345 | B2 | 5/2004 |
| JP | 2006323833 | A | 11/2006 |
| JP | 2009007302 | A | 1/2009 |
| JP | 2010198561 | A | 9/2010 |
| KR | 1020150008179 | A | 1/2015 |

OTHER PUBLICATIONS

Geoffroy Hautier, Chris Fischer, Virginie Ehrlacher, Anubhav Jain, and Gerbrand Ceder, "Data Mined Ionic Substitutions for the Discovery of New Compounds", 2011, Inorg. Chem. 2011, 50, pp. 656-663. (Year: 2011).*

Jihyun Shim and Alexander D. MacKerell Jr., "Computational ligand-based rational design: Role of conformational sampling and force fields in model development", 2012, Medchemcomm 2(5). pp. 356-370. (Year: 2012).*

Developing Virtual Screening Technology Using PC Distributed Computing; Korea Institute of Science and Technology Information; Dec. 10, 2003; 40 pages.

Search Report for KR Application No. 10-2015-0154676, Filing Date Nov. 4, 2015; dated Aug. 14, 2015; 14 pages.

Daniel S. Murrell, et al., "Chemically Aware Model Builder (camb): an R package for property and bioactivity modelling of small molecules", JCheminform, (2015), vol. 7, No. 45, pp. 1-10.

Extended European Search Report—European Patent Application No. 16195276.7 dated Apr. 21, 2017.

Jerome G. P. Wicker et al., "Will it crystallise? Predicting crystallinity of molecular materials", CrystEngComm, (Mar. 7, 2015), vol. 17, No. 9, pp. 1893-2052.

Japanese Office Action for JP Application No. 2016-215596 dated Aug. 18, 2020.

Chinese Office Action-Chinese Patent Application No. 2016109588963 dated Feb. 18, 2021, citing references listed within.

* cited by examiner

METHOD AND DEVICE FOR SEARCHING NEW MATERIAL

CROSS-REFERENCE TO RELATED APPLICATION

This application claims priority to Korean Patent Application No. 10-2015-0154676 filed on Nov. 4, 2015, and all the benefits accruing therefrom under 35 U.S.C. § 119, the content of which in its entirety is herein incorporated by reference.

BACKGROUND

(a) Field

Embodiments of the invention relate to a device and method for searching a new material for developing a material with improved properties.

(b) Description of the Related Art

Material simulation techniques, such as the first principle simulation theory and super computers for improving calculation performance, have been applied to a process for developing advanced materials that used to depend upon experiments. Such material simulation techniques may include the high throughput screening ("HTS") for generating a plurality of virtual materials, and selecting candidate materials for the advanced materials from among the virtual materials generated through computer simulation.

The virtual material is generated by a combination of a plurality of partial structures in the HTS, so the number of the virtual materials that are generated according to the number of partial structures or the combination method of the partial structures exponentially increases. Conventionally, a simulation of one virtual material may take more than several hours, so when the number of the virtual materials to be simulated increases, the entire virtual materials may not be effectively estimated through simulation.

Therefore, methods for selecting a material group with likelihood in advance to simulation have been researched by applying a scheme such as a machine learning without screening the entire virtual materials through simulation. The machine learning signifies a methodology for configuring a model for solving a given problem based on known data, and when the machine learning is applied, the simulation result may be quickly expected without any simulation through a machine learning model by use of generally known physical property calculated (or measured) data. Hence, a further more number of candidate materials may be estimated.

The above information disclosed in this Background section is only for enhancement of understanding of the background of the invention and therefore it may contain information that does not form the prior art that is already known in this country to a person of ordinary skill in the art.

SUMMARY

When methods for selecting a material group with likelihood in advance to simulation by applying a scheme such as a machine learning are used, the method for applying the machine learning to the high throughput screening ("HTS") may be desired to generate a lot of virtual materials to generate advanced material candidate materials, so the materials with undesired properties may be mass produced, such that the candidate material of advanced materials may not be effectively searched.

Exemplary embodiments of the invention relate to a device and method for searching a new material based upon a probability function with structure information and physical property information of a material as a variable.

Exemplary embodiments of the invention relate to a device and method for acquiring a physical property of a specific material based on a probability function with structure information and physical property information of a material as a variable.

According to an exemplary embodiment of the invention, a method for searching a new material includes: performing a learning on a material model, which is modeled based on a known material; determining a candidate material by inputting a targeted physical property to a result of the learning; and determining the new material from the candidate material.

In an exemplary embodiment, the performing the learning on the material model may include: modeling the material model based upon first structure information, which is information on a structure of the known material, first physical property information, which is information on a physical property of the known material, information on a potential fact, and a learning parameter; updating the learning parameter; and determining whether to finish the learning based on an update result of the learning parameter.

In an exemplary embodiment, the first structure information may include information on a partial structure in a molecular structure of the material.

In an exemplary embodiment, the first structure information may include information on atoms in the molecular structure of the material and information on a combination of the atoms.

In an exemplary embodiment, the first structure information may include two-dimensional image information on the molecular structure of the material.

In an exemplary embodiment, the learning parameter may include at least one of a default value parameter on the structure of the material, a default value parameter on a physical property of the material, a default value parameter of the potential fact, a relationship parameter between the structure of the material and the potential fact, and a relationship parameter between the physical property of the material and the potential fact, and the performing the learning may further include resetting the learning parameter with a random value before the modeling.

In an exemplary embodiment, the modeling the material model may include: modeling an energy function based on the first structure information, the first physical property information, and the learning parameter; and generating second structure information, which is information on a structure of the new material, and second physical property information, which is information on a physical property of the new material, based on a probability function of the material model deduced based on the energy function.

In an exemplary embodiment, the updating the learning parameter may include updating the learning parameter based on a free energy function of the material model deduced based on the probability function and the energy function.

In an exemplary embodiment, the updating the learning parameter based on the probability function and the free energy function may include updating the learning parameter by using a difference between the learning parameter and an objective function expressed as the free energy function.

In an exemplary embodiment, the objective function may represent a function deduced from a differential expression of the probability function. In an exemplary embodiment, the determining the new material from the candidate material may include verifying at least one of physical validity, chemical stability and easiness of synthesis of the candidate material; and determining the verified candidate material from the candidate material to be the new material.

According to another embodiment of the invention, a device for searching a new material includes: a learning performer which performs a learning on a material model, which is modeled based on a known material; and a new material determiner which determines a candidate material by inputting a targeted physical property to a result of the learning, and determining the new material from the candidate material.

In an exemplary embodiment, the learning performer may include: a material modeler which models the material model based on first structure information, which is information on a structure of the known material, first physical property information, which is information on a physical property of the known material, information on a potential fact, and a learning parameter; a parameter updater which updates the learning parameter; and a learning performance finisher which determines whether to finish the learning based on an update result of the learning parameter.

In an exemplary embodiment, the first structure information may include information on a partial structure in a molecular structure of the material.

In an exemplary embodiment, the first structure information may include information on atoms in the molecular structure of the material and information on a combination of the atoms.

In an exemplary embodiment, the first structure information may include two-dimensional image information on the molecular structure of the material.

In an exemplary embodiment, the learning parameter may include at least one of a default value parameter on the structure of the material, a default value parameter on a physical property of the material, a default value parameter of the potential fact, a relationship parameter between the structure of the material and the potential fact, and a relationship parameter between the physical property of the material and the potential fact, and the material modeler may reset the learning parameter with a random value before the modeling. In an exemplary embodiment, the material modeler may model an energy function based on the first structure information, the first physical property information, and the learning parameter, and may generate second structure information, which is information on a structure of the new material, and second physical property information, which is information on a physical property of the new material, based on a probability function of the material model deduced based on the energy function.

In an exemplary embodiment, the parameter updater may update the learning parameter based on a free energy function of the material model deduced based on the probability function and the energy function.

In an exemplary embodiment, the parameter updater may update the learning parameter by using a difference between the learning parameter and an objective function expressed as the free energy function.

In an exemplary embodiment, the objective function may rea function deduced from a differential expression of the probability function.

In an exemplary embodiment, the new material determiner may verify at least one of physical validity, chemical stability, and easiness of synthesis of the candidate material, and may determine the verified candidate material from the candidate material to be the new material.

BRIEF DESCRIPTION OF THE DRAWINGS

These and/or other features of the invention will become apparent and more readily appreciated from the following detailed description of embodiments thereof, taken in conjunction with the accompanying drawings, in which.

DETAILED DESCRIPTION

Figure 1:
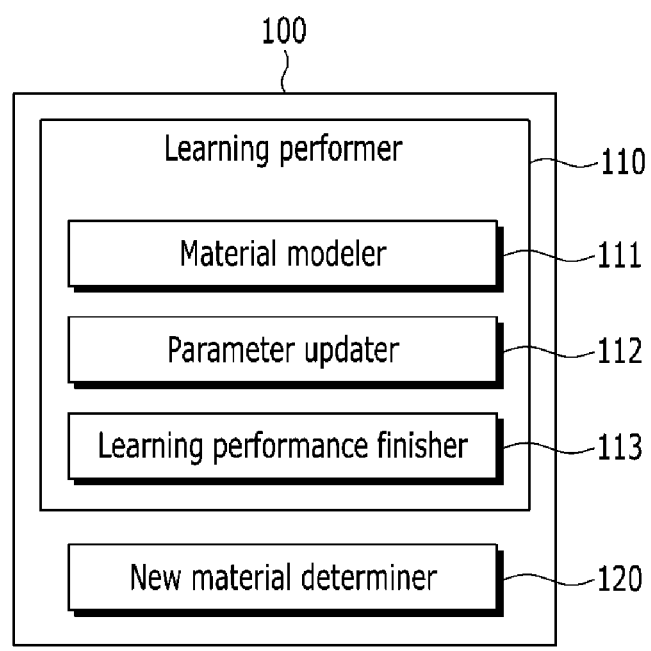
FIG. 1 shows a block diagram of an exemplary embodiment of a device for searching a material according to the invention.

In the following detailed description, only certain exemplary embodiments of the invention have been shown and described, simply by way of illustration. As those skilled in the art would realize, the described embodiments may be modified in various different ways, all without departing from the spirit or scope of the invention. Accordingly, the drawings and description are to be regarded as illustrative in nature and not restrictive and like reference numerals designate like elements throughout the specification.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. In addition, unless explicitly described to the contrary, the word "comprise" and variations, such as "comprises" or "comprising," will be understood to imply the inclusion of stated elements but not the exclusion of any other elements. Further, in the specification, the word "on" means positioning on or below the object portion, but does not essentially mean positioning on the upper side of the object portion based on a gravity direction.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinafter, exemplary embodiments of a device and method for searching a new material will be described in detail with reference to the accompanying drawings.

FIG. 1 shows a block diagram of an exemplary embodiment of a device for searching a material according to the invention.

Referring to FIG. 1, an exemplary embodiment of the device 100 for searching a material (e.g., a material with a desired property) includes a learning performer 110 that performs a machine learning on a material model, and a new material determiner 120 that determines a new material corresponding to a targeted property (e.g., a targeted physical property). The learning performer 110 includes a material modeler 111 that models a material model using a learning parameter, a parameter updater 112 that updates the learning parameter used for modeling the material model, and a learning performance finisher 113 that determines whether to finish the learning or the operation of the learning performer 110 based on an update result of the learning parameter.

In an exemplary embodiment, the learning performer 110 performs a learning on a material model, and the material model may be modeled by the material modeler 111 based on structure information (x), which is information on a structure of a known material, physical property information (y), which is information on a physical property of the known material, a potential variable h for indicating a potential fact, and a learning parameter. In an exemplary embodiment, the structure information may include two-dimensional image information on the molecular structure of the material. In an exemplary embodiment, the structure information may include information on atoms in the molecular structure of the material, and information on a combination of the atoms. In such an embodiment, the material modeler 111 may model an energy function, in which structure information of the material, physical property information of the material and the potential fact are connected through the learning parameter, as the material model. The structure information and the physical property information of the known material may be stored in a database 130.

The parameter updater 112 updates the learning parameter used for modeling the material model by calculating a variation of a free energy function of the material model.

The learning performance finisher 113 determines whether to finish the learning when the learning on a material model has been performed in some measure or a predetermined number of times.

In an exemplary embodiment, the new material determiner 120 inputs or substitutes a targeted physical property for the learned material model to determine a new material to be searched. In an alternative exemplary embodiment, the new material determiner 120 may acquire physical property information of a specific material by substituting the learned material model with structure information of the specific material.

In an exemplary embodiment, the learning performer 110 and the new material determiner 120 may be implemented by a processor and a memory.

An exemplary embodiment of a method for the device for searching a material to search a new material will now be described with reference to FIG. 2 to FIG. 4.

Figure 2:
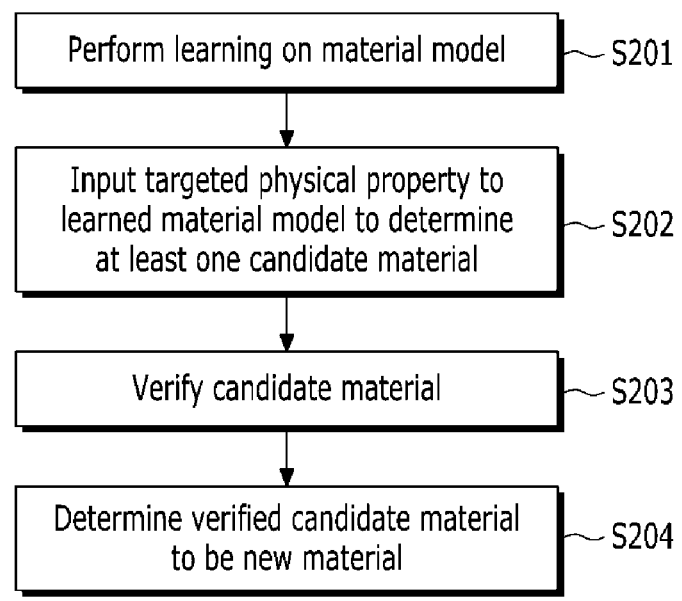
FIG. 2 shows a flowchart of an exemplary embodiment of a method for searching a material according to the invention.
Figure 3:
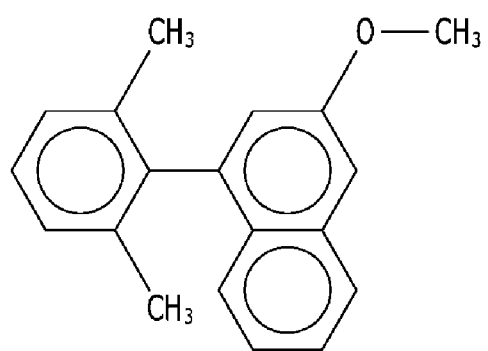
FIG. 3 shows a structure of an exemplary embodiment of a known organic material according to the invention.
Figure 4:
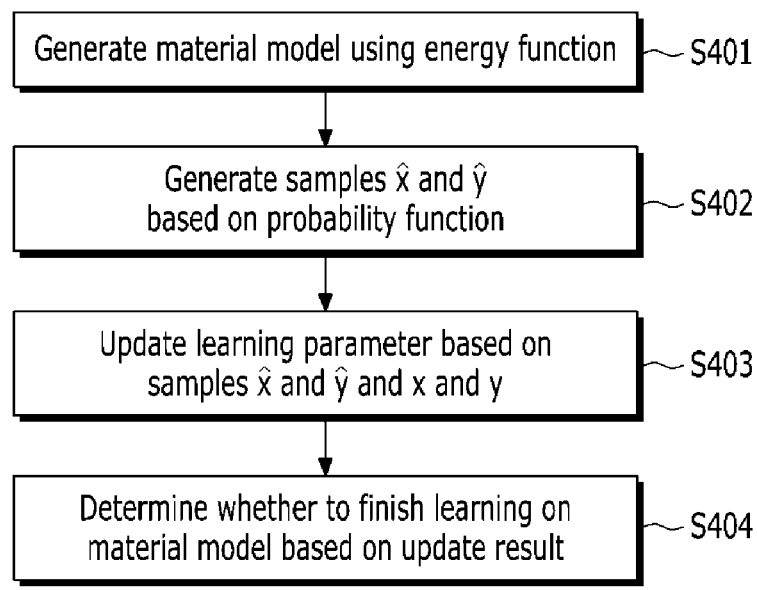
FIG. 4 shows a flowchart of an exemplary embodiment of a method for learning a material model according to the invention.

FIG. 2 shows a flowchart of an exemplary embodiment of a method for searching a material according to the invention, FIG. 3 shows a structure of an exemplary embodiment of a known organic material according to the invention, and FIG. 4 shows a flowchart of an exemplary embodiment of a method for learning a material model according to the invention.

Referring to FIG. 2, an exemplary embodiment of a method for searching a material includes performing a learning on a material model (S201). In an exemplary embodiment, the device for searching a material performs the learning on the material model. According to an exemplary embodiment, the device for searching a material may perform the learning on a material model according to a method to be described below. An exemplary embodiment of a method for learning a material model will now be described in detail with reference to FIG. 4.

An exemplary embodiment of a method for learning a material model includes generating a material model using energy function (S401). In an exemplary embodiment, the device for searching a material may model a material model. In such an embodiment, to model a material model, the device for searching a material reads structure information (x) on a structure of a known material and physical property information (y) on a physical property of the material from a database.

In an exemplary embodiment, the device for searching a material may perform the leering on the material model for around 50,000 organic materials. The device for searching a material reads the structure information (x) on a structure of known 50,000 organic materials and the physical property information (y) on a physical property of each organic material from the database.

In an exemplary embodiment, the structure information (x) may be expressed in a sequence of a number indicating existence and inexistence of a part structure. The part structure is a part of the known material structure. For example, the part structure group may include a single hexagonal ring, a double hexagonal ring, a triple hexagonal ring, and so on. The sequence of the number of the part structure may be a binary sequence. Therefore, the known organic material showed in FIG. 3 may be expressed [1, 1, 0]. For example, the part structures may be obtained by software or hardware performing a circular fingerprint method.

In an exemplary embodiment, the physical property information (y) may be obtained by a computer simulation. For example, about 50,000 light receiving intensity/luminescence intensity corresponding to the 50,000 organic materials may be calculated by the computer simulation. The calculation accuracy may increase by transforming the dimension of the physical property information into a log scale because a specific physical property value for most organic materials may be calculated with approximately zero.

The device for searching a material resets a learning parameter for modeling a material model with a random value based on the structure information (x) and the physical property information (y). The learning parameter includes a default value parameter (a) on a structure of a material, a default value parameter (b) on a physical property of the material, a default value parameter (c) on a potential fact, a relationship parameter (U) between the structure of the material and the potential fact, and a learning parameter (v)

between the physical property of the material and the potential fact. In such an embodiment, the learning parameter θ may be expressed in Equation 1.

$$\theta = \{U, v, a, h, c\} \quad \text{(Equation 1)}$$

The device for searching a material simulates an energy function based on a variable x for indicating structure information of the material, a variable y for indicating physical property information of the material, a potential variable h for representing the potential fact, and a learning parameter to thereby generate a material model (S401). According to an exemplary embodiment, the energy function with the variables x, y and h may be expressed in Equation 2.

$$E(x, y, h) = E(x, h) + E(y, h) + E(x) + E(y) + E(h) \quad \text{(Equation 2)}$$
$$= -h^T U x - \lambda h^T v y - a^T x + \frac{\lambda}{2}(y-b)^2 - c^T h$$

In Equation 2, x and h are vectors, and y is a real number. E(x, h) indicates the energy determined by the variable x and defined based on the learning parameter U and the potential variable h, and E(y, h) indicates the energy determined by the variable y and defined based on the learning parameter v and the potential variable h. A denotes a designated parameter and relates to a learning accuracy and a learning speed on the material model. E(x) indicates energy determined by the variable x and defined based on the parameter a, E(y) indicates energy determined by the variable y and defined based on the parameter b, and E(c) indicates energy determine by the variable h and defined based on the parameter c.

In one exemplary embodiment, for example, when the database stores molecular structure information of a material as structure information of the material and energy band-gap information of the material as physical property information of the material, molecular structure information may be used as the variable x and energy band-gap information may be used as the variable y. In such an embodiment, a method, in which a position of a specific part structure in a molecular structure of the material is expressed to be 0 or 1 as the variable x, may be used.

A probability function of the material model and a free energy function of the material model may be deduced from the energy function of the material model. Equation 3 expresses a probability function of the material model according to an exemplary embodiment.

$$p(x, y, h) = \frac{\exp\{-E(x, y, h)\}}{\sum_{x,h} \int_y \exp\{-E(x, y, h)\} dy} \quad \text{(Equation 3)}$$
$$= \frac{1}{Z} \exp\{-E(x, y, h)\}$$

The variable h on the potential fact in the probability function of Equation 3 shows an unobserved variable, so when the variable h is marginalized out from Equation 3, the probability h of the material model on the known x and y may be expressed as in Equation 4.

$$p(x, y) = \quad \text{(Equation 4)}$$
$$\frac{1}{Z} \exp\left\{a^T x - \frac{\lambda}{2}(y-b)^2 + \sum_i \text{softplus}(U_i \cdot x + \lambda y v_i + c_i)\right\}$$

Here, "softplus" function is expressed in Equation 5.

$$\text{softplus}(x) \equiv \log(1 + \exp(x)) \quad \text{(Equation 5)}$$

An exemplary embodiment of a method for searching a material includes generating samples $\hat{x}$ and $\hat{y}$ of a new material based on the probability function of the material model (S402). In an exemplary embodiment, the device for searching a material may generate the samples $\hat{x}$ and $\hat{y}$ of the new material based on the probability function of the material model. A conditional probability of the variable h for the variable x and the variable y may be calculated according to Equation 6.

$$p(h_j=1|x,y) = \text{sigm}(U_j.x + \lambda v_j y + c_j) \quad \text{(Equation 6)}$$

Here the "sigm" function signifies a sigmoid function and is expressed in Equation 7.

$$\text{sigm}(x) \equiv \frac{1}{1 + \exp(x)} \quad \text{(Equation 7)}$$

The device for searching a material determines the variable h using Equation 6 and deducts the samples $\hat{x}$ and $\hat{y}$ based on the conditional probability of the variable x and the variable y for the variable h. Equation 8 expresses the conditional probability of the variable x for the variable h, and Equation 9 expresses the conditional probability of the variable y for the variable h.

$$p(x_i = 1 | h) = \frac{1}{1 + \exp\{-h^T U_{\cdot i} - a_i\}} \quad \text{(Equation 8)}$$

$$p(y | h) = \mathcal{N}(y | b + h^T v, \lambda) \quad \text{(Equation 9)}$$

In Equation 9, N (x|m, s) is a normal distribution for the variable x with the mean m and the dispersion s. The device for searching a material may generate the samples $\hat{x}$ and $\hat{y}$ based on the probability distribution of the variable x and the variable y of Equation 8 and Equation 9. In an exemplary embodiment, the generated samples $\hat{x}$ and $\hat{y}$ may be input to the energy function of Equation 2, and other samples $\hat{x}$ and $\hat{y}$ may be regenerated when the samples $\hat{x}$ and $\hat{y}$ are input to the energy function of Equation 2. In such an embodiment, generations and inputs of the samples $\hat{x}$ and $\hat{y}$ may be repeated by a predetermined number of times according to a setting of the device for searching a material.

The device for searching a material updates the learning parameter θ based on x and y and the samples $\hat{x}$ and $\hat{y}$. When the learning parameter θ is updated, an objective function expressed as the free energy function of the material model may be used. First, the device for searching a material substitutes the objective function with x and y and the samples $\hat{x}$ and $\hat{y}$ or inputs x and y and the samples $\hat{x}$ and $\hat{y}$ to the objective function, to calculate the free energy variation of the material model.

Equation 10 expresses an objective function for finding the free energy variation of the material model according to an exemplary embodiment.

$$\frac{\partial \mathcal{H}}{\partial \theta} = (1+\alpha)\frac{\partial \mathcal{F}(x, y)}{\partial \theta} - \frac{\partial \mathcal{F}(x, \hat{y})}{\partial \theta} - \alpha \frac{\partial \mathcal{F}(\hat{x}, \hat{y})}{\partial \theta} \quad \text{(Equation 10)}$$

Here, $\mathcal{F}(x, y)$ is a free energy function of the material model, and a is a designated parameter relating to a learning accuracy. In an exemplary embodiment, the objective function of Equation 10 may be a combination of variations of a plurality of free energy functions for the material model. The free energy function of the material model may be expressed as Equation 11 from the energy function.

$$\mathcal{F}(x, y) = -\log \sum_{h} \exp\{-E(x, y, h)\} \quad \text{(Equation 11)}$$

Therefore, a relationship between the free energy function of the material model and the probability function of the material model may be expressed as in Equation 12.

$$p(x, y) = \frac{1}{Z}\exp\{-\mathcal{F}(x, y)\} \quad \text{(Equation 12)}$$

In an exemplary embodiment, the objective function may be deduced from a differential expression of the probability function of the material model. The learning on the material model may be performed to maximize the likelihood for the given data (x and y). In such an embodiment, where a negative logarithm (−log) of the probability function is used, a minimum value of the negative logarithm (−log) of the probability function is determined by a differential expression on the negative logarithm of the probability function so the learning parameter may be updated to maximize the likelihood. In such an embodiment, the differential expression on the learning parameter of the negative logarithm of the probability function may be used as the objective function for calculating the variation of the learning parameter of the free energy.

In an exemplary embodiment, a generative objective function deduced based on the probability function of the material model is expressed in Equation 13.

$$-\frac{\partial \log p(x, y)}{\partial \theta} \approx \frac{\partial \mathcal{F}(x, y)}{\partial \theta} - \frac{\partial \mathcal{F}(\hat{x}, \hat{y})}{\partial \theta} \quad \text{(Equation 13)}$$

In an alternative exemplary embodiment, a discriminative objective function deduced based on a conditional probability function of the material model is expressed in Equation 14.

$$-\frac{\partial \log p(y \mid x)}{\partial \theta} \approx \frac{\partial \mathcal{F}(x, y)}{\partial \theta} - \frac{\partial \mathcal{F}(x, \hat{y})}{\partial \theta} \quad \text{(Equation 14)}$$

The objective function of Equation 10 may be a hybrid objective function that is a linear combination of a generative objective function and a discriminative objective function. In an exemplary embodiment, the generative objective function of Equation 13 is linearly combined to the discriminative objective function of Equation 14 through a designated parameter a for indicating a weight value to thus deduct the hybrid objective function of Equation 10.

An exemplary embodiment of a method for searching a material includes updating the learning parameter based on the samples $\hat{x}$ and $\hat{y}$, and x and y (S403). In an exemplary embodiment, the device for searching a material may update the learning parameter according to Equation 15.

$$\theta \leftarrow \theta - \varepsilon \frac{\partial \mathcal{H}}{\partial \theta} \quad \text{(Equation 15)}$$

In Equation 15, c is a designated parameter relating to a learning speed of the material model.

An exemplary embodiment of a method for searching a material includes determining whether to finish the learning on a material model based on an update result of the learning parameter (S404). In an exemplary embodiment, the device for searching a material may determine whether to finish the learning on a material model based on an update result of the learning parameter. According to an exemplary embodiment, when the learning parameter is updated for a predetermined number of times or the variation of the free energy of the material model does not become greater (or becomes less) than a predetermined value, the device for searching a material may finish the learning on the material model.

In an exemplary embodiment, the method for searching a material includes inputting or substituting a targeted physical property for the learned material model to determine at least one candidate material (S202) when the learning on the material model is finished as described above. In an exemplary embodiment, the device for searching a material may substitute a targeted physical property for the learned material model to determine at least one candidate material.

According to an exemplary embodiment, the conditional probability on the targeted physical property y is calculated using Equation 16.

$$p(h_j = 1 \mid y) = sigm(\lambda v_j y + c_j) \quad \text{(Equation 16)}$$
$$= \frac{1}{1 + \exp\{-\lambda v_j y + c_j\}}$$

The potential variable h is randomly generated through the conditional probability function of Equation 16. A probability function of a structure of a candidate material of a new material is calculated using the generated potential variable h, as expressed in Equation 17.

$$p(x_i = 1 \mid h) = \frac{1}{1 + \exp\{-h^T U_{\cdot i} - a_i\}} \quad \text{(Equation 17)}$$

At least one candidate material may be determined based on the probability function on the structure of the candidate material expressed in Equation 17. In an exemplary embodiment, the method for searching a material includes verifying the candidate material (S203). In an exemplary embodiment, the device for searching a material may verify physical validity, chemical stability, and easiness of synthesis of at least one candidate material. In an exemplary embodiment, the method for searching a material includes determining the verified candidate material from among at least one candidate material to be a new material (S204). In an exemplary embodiment, the device for searching a material may determine the verified candidate material from among at least one candidate material to be a new material.

In an alternative exemplary embodiment, when structure information of the specific material is known, the device for searching a material may acquire the physical property of the specific material by substituting the learned material model with the structure information of the specific material or by inputting the structure information of the specific material to the learned material model.

Figure 5:
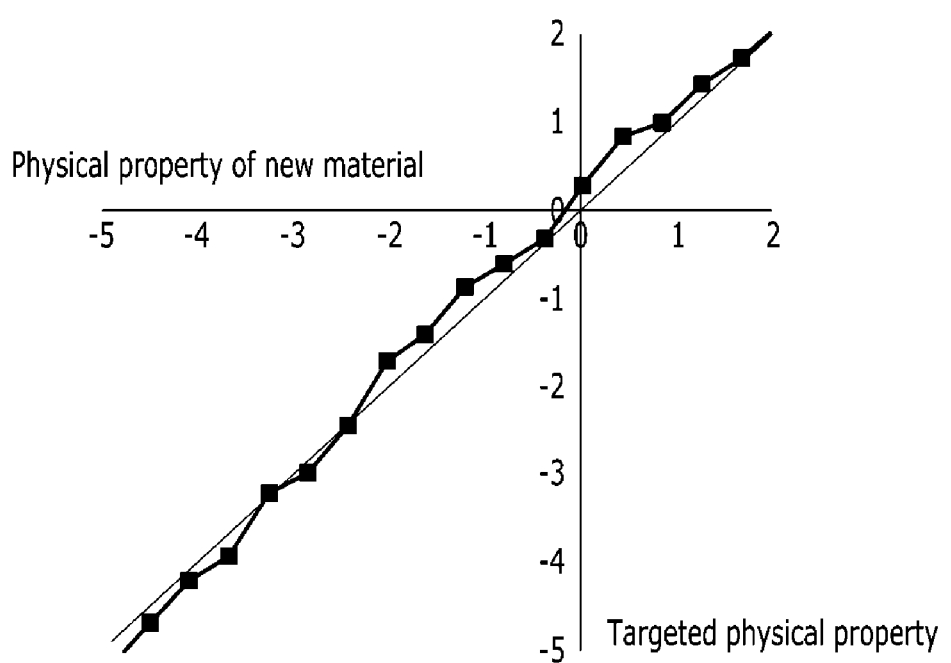
FIG. 5 shows a graph of a material search result according to an exemplary embodiment.

FIG. 5 shows a graph of a material search result according to an exemplary embodiment.

Regarding the graph of FIG. 5, a vertical axis represents the targeted physical property, and a horizontal axis indicates the physical property of the new material determined according to an exemplary embodiment. Referring to FIG. 5, it is found that the relationship between the targeted physical property and the physical property of the new material determined according to an exemplary embodiment closely corresponds to each other. As shown in FIG. 5, the new material with the physical property that is very close to the targeted physical property, which is input to the device for searching a material to search a new material, may be effectively searched through an exemplary embodiment of the method for searching a material.

Figure 6:
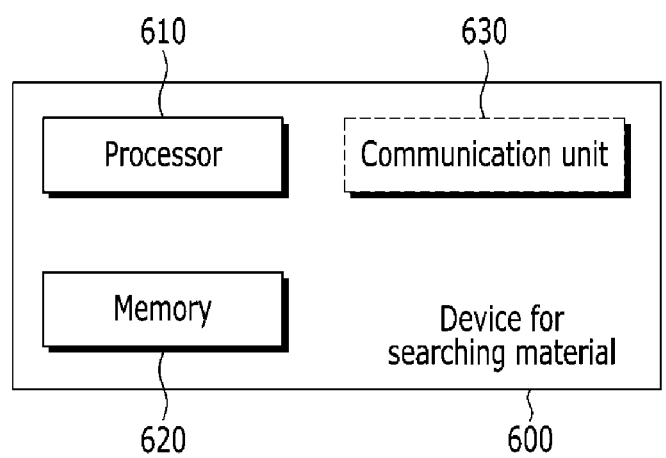
FIG. 6 shows a block diagram of an alternative exemplary embodiment of a device for searching a material according to the invention.

FIG. 6 shows a block diagram of an alternative exemplary embodiment of a device for searching a material according to the invention.

An exemplary embodiment of the device for searching a material 600 includes a processor 610 and a memory 620. The device for searching a material 600 may include a communication unit 630 for performing a wired and wireless communication with another device. The memory 620 may be connected to the processor 610 to store various sorts of information for driving the processor 610 or at least one program executed by the processor 610. The communication unit 630 may be connected to the processor 610 to transmit and receive a radio signal. The processor 610 may perform a function, a process, or a method according to an exemplary embodiment of the invention described herein. An operation of the device for searching a material 600 according to an exemplary embodiment may be realized by the processor 610.

In an exemplary embodiment of the invention, the memory may be provided inside or outside the processor, and the memory may be connected to the processor by using various means known to a person skilled in the art. The memory is a volatile or non-volatile storage medium in various formats, and for example, the memory may include a read-only memory ("ROM") or a random access memory ("RAM").

While the invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method for searching a material having a targeted physical property using a high-throughput screening, the method comprising:
performing a learning on a material model which is modeled based on a known material;
determining a candidate material by inputting the targeted physical property to a result of the learning; and
determining the material having the targeted physical property from the candidate material,
wherein the performing the learning on the material model comprises:
modeling the material model based upon first structure information, which is information on a structure of the known material, first physical property information, which is information on a physical property of the known material, information on a potential factor, and a learning parameter,
wherein the learning parameter comprises at least one of a default value parameter on the structure of the known material, a default value parameter on a physical property of the known material, a default value parameter of the potential factor, a relationship parameter between the structure of the known material and the potential factor, and a relationship parameter between the physical property of the known material and the potential factor, and
wherein the modeling the material model comprises:
determining a probability function of the material model from an energy function based on the first structure information, the first physical property information, and the learning parameter; and
generating second structure information, which is information on a structure of the material having the targeted physical property, and second physical property information, which is information on a physical property of the material having the targeted physical property, based on the probability function of the material model.

2. The method of claim 1, wherein
the performing the learning on the material model further comprises:
updating the learning parameter; and
determining whether to finish the learning based on an update result of the learning parameter.

3. The method of claim 2, wherein
the first structure information comprises information on a partial structure in a molecular structure of the known material.

4. The method of claim 2, wherein
the first structure information comprises:
information on atoms in the molecular structure of the known material; and
information on a combination of the atoms.

5. The method of claim 2, wherein
the first structure information comprises two-dimensional image information on the molecular structure of the known material.

6. The method of claim 2, wherein
the performing the learning on the material model further includes
resetting the learning parameter with a random value before the modeling.

7. The method of claim 2, wherein
the updating the learning parameter comprises:
updating the learning parameter based on a free energy function of the material model deduced based on the probability function and the energy function.

8. The method of claim 7, wherein
the updating the learning parameter based on the probability function and the free energy function comprises:
updating the learning parameter by using a difference between the learning parameter and an objective function expressed as the free energy function.

9. The method of claim 8, wherein
the objective function represents a function deduced from a differential expression of the probability function.

10. The method of claim 1, wherein
the determining the material having the targeted physical property among the candidate material comprises:
verifying at least one of physical validity, and chemical stability the candidate material; and
determining the verified candidate material from the candidate material to be the material having the targeted physical property.

11. A device for searching a material as a device for searching an advance material having a targeted physical property using a high-throughput screening, the device comprising a processor, wherein the processor includes:
a learning performer which performs a learning on a material model that is modeled based on a known material; and
a material determiner which determines a candidate material by inputting a targeted physical property to a result of the learning, and determines a material having the targeted physical property the candidate material,
wherein the learning performer comprises:
a material modeler which models the material model based on first structure information, which is information on a structure of the known material, first physical property information, which is information on a physical property of the known material, information on a potential factor, and a learning parameter,
wherein the learning parameter comprises at least one of a default value parameter on the structure of the known material, a default value parameter on a physical property of the known material, a default value parameter of the potential factor, a relationship parameter between the structure of the known material and the potential factor, and a relationship parameter between the physical property of the known material and the potential factor, and
wherein the material modeler determines a probability function of the material model from an energy function based on the first structure information, the first physical property information, and the learning parameter, and generates second structure information, which is information on a structure of the material having the targeted physical property, and second physical property information, which is information on a physical property of the material having the targeted physical property, based on the probability function of the material model.

12. The device of claim 11, wherein
the learning performer further comprises:
a parameter updater which updates the learning parameter; and
a learning performance finisher which determines whether to finish the learning based on an update result of the learning parameter.

13. The device of claim 12, wherein
the first structure information comprises information on a partial structure included in a molecular structure of the known material.

14. The device of claim 12, wherein
the first structure information comprises information on atoms in the molecular structure of the known material and information on a combination of the atoms.

15. The device of claim 12, wherein
the first structure information comprises two-dimensional image information on the molecular structure of the known material.

16. The device of claim 12, wherein
the material modeler resets the learning parameter with a random value before the modeling.

17. The device of claim 12, wherein
the parameter updater updates the learning parameter based on a free energy function of the material model deduced based on the probability function and the energy function.

18. The device of claim 17, wherein
the parameter updater updates the learning parameter by using a difference between the learning parameter and an objective function expressed as the free energy function.

19. The device of claim 18, wherein
the objective function represents a function deduced from a differential expression of the probability function.

20. The device of claim 11, wherein
the material determiner verifies at least one of physical validity, and chemical stability of the candidate material, and determines the verified candidate material from the candidate material to be the material having the targeted physical property.

* * * * *